United States Patent [19]
Chabardès et al.

[11] 3,981,900
[45] Sept. 21, 1976

[54] PREPARATION OF ALIPHATIC DINITRILES

[75] Inventors: Pierre Chabardès, Lyon; Pierre Gandilhon, Charly; Charles Grard, Lyon; Michel Thiers, Rhone, all of France

[73] Assignee: Rhone-Poulenc S.A., Paris, France

[22] Filed: Apr. 30, 1971

[21] Appl. No.: 139,204

Related U.S. Application Data

[63] Continuation of Ser. No. 738,838, June 21, 1968, abandoned.

[30] Foreign Application Priority Data

June 22, 1967  France .............................. 67.111536

[52] U.S. Cl. ............................................. 260/465.8 D
[51] Int. Cl.$^2$ ............... C07C 120/00; C07C 121/20; C07C 121/26
[58] Field of Search .............................. 260/465.8 D

[56] References Cited

UNITED STATES PATENTS

| | | | |
|---|---|---|---|
| 3,459,785 | 8/1969 | Jones | 260/465.8 D |
| 3,562,181 | 2/1971 | Linn et al. | 260/465.8 D |

FOREIGN PATENTS OR APPLICATIONS

| | | | |
|---|---|---|---|
| 1,451,443 | 7/1966 | France | 260/465.8 D |
| 1,472,033 | 1/1967 | France | 260/465.8 D |
| 6,603,115 | 9/1966 | Netherlands | 260/465.8 D |
| 1,177,059 | 1/1970 | United Kingdom | 260/465.8 D |

*Primary Examiner*—Joseph Paul Brust
*Attorney, Agent, or Firm*—Stevens, Davis, Miller & Mosher

[57] ABSTRACT

The addition of a free metal of group VIII of the Periodic Table or of one of its oxides or hydroxides to acrylonitrile heated under a hydrogen pressure of 1 to 50 bars in the presence of a ruthenium derivative as catalyst improves the rate of conversion of the acrylonitrile into 1,4-dicyanobutenes and/or adiponitrile.

9 Claims, No Drawings

PREPARATION OF ALIPHATIC DINITRILES

This application is a continuation of Ser. No. 738,838, filed June 21, 1968, and now abandoned.

The present invention relates to the preparation of 1,4-dicyano-butenes and/or of adiponitrile by dimerisation of acrylonitrile.

In our U.S. Ser. No. 535,322 now U.S. Pat. No. 3,671,569 we have described and claimed a process for the preparation of 1,4-dicyano-butenes and/or of adiponitrile which consists of heating acrylonitrile, e.g. to 50° to 150°C., under a hydrogen pressure of 1 to 50 bars in the presence of, as catalyst an organic or inorganic ruthenium derivative.

In this process the degree of formation of 1,4-dicyano-butenes or of adiponitrile is controlled by the working conditions and the catalyst used. A judicious choice of these conditions makes it possible to cause the reaction to produce a preponderant amount of one or the other of the two products and also makes it possible to reduce the formation of propionitrile produced by the hydrogenation of the acrylonitrile. The catalysts which are especially useful in this process are the inorganic and organic derivatives of ruthenium and the chelates and complexes of ruthenium with electron donors.

It has now been found, and it is this which forms the subject of the present invention, that the aforesaid process for the preparation of 1,4-dicyano-butenes and/or of adiponitrile from acrylonitrile by heating acrylonitrile under a hydrogen pressure of 1 to 50 bars in the presence of catalytic quantities of an inorganic or organic derivative of ruthenium, may be improved by adding to the reaction mixture a free metal of group VIII of the Periodic Table or one of its oxides or hydroxides. These latter compounds activate the catalyst and the speed of the reaction varies as a function of their concentration. This increase in the speed of the reaction shows itself in an increase in the degree of conversion of acrylonitrile within a given time, with the yields of dimers and/or hydrodimer remaining approximately constant. The use of these activators thus allows the productivity of the equipment to be increased by increasing the amount of dimers and/or of hydrodimers produced within a given time, or by reducing the dwell time of the reagents in the equipment for producing a given quantity of dimers and/or of hydrodimer. Furthermore the activator makes it possible to increase the production of the hydrodimer when the reaction is carried out under the conditions for preferential formation of the hydrodimer.

Amongst the metals of group VIII which are more particularly suitable as activators in the process of the invention, ruthenium, platinum, nickel and rhodium are preferred. These metals may or may not be deposited on an inert carrier such as carbon black, silica or alumina. $Ru(OH)_3$, $Ru\ O(OH)_2$ and $Ru\ O_2$ may be quoted as examples of preferred oxides and hydroxides of group VIII.

The quantity of activator employed varies with the nature and quantity of the catalyst used and with the nature of the activator. Though it is possible to use quantities of activator which introduce a quantity of metal into the reaction medium which is greater than that introduced by the catalyst, it is preferable to restrict the quantity of activator to an amount such that the weight of metal is at most equal to the weight of metal introduced by the catalyst. When the metal introduced in the activator is a particularly efficient hydrogenation catalyst, the quantity of activator is chosen so as materially to increase the speed of the dimerisation and hydrodimerisation reaction without at the same time causing substantial hydrogenation of acrylonitrile to propionitrile. A quantity of activator such as to introduce a weight of metal which is at most equal to 25% (e.g. 1 to 25%) of that introduced by the catalyst is generally sufficient.

The catalysts used in the process of the invention are inorganic and organic derivatives of ruthenium such as the halides, the thiocyanates, the salts of oxygen-containing inorganic acids such as the sulphates, the nitrates, the oxyhalides and hydroxyhalides, and the salts of aliphatic, cycloaliphatic or aromatic organic acids such as the acetate, oxalate, stearate or naphthenate. The alcoholates and the phenates may also be used. Suitable other inorganic and organic ruthenium compounds include the alkali metal and alkaline earth metal ruthenates, the mixed salts of ruthenium and an alkali metal, such as the sodium or potassium halogenoruthenates, and the halogenated or nitrosylated or aminated derivatives such as nitrosochloro-ruthenium or trichlororuthenium-hexamine. Chelates such as the acetylacetonates, optionally substituted by, for example, aliphatic or cycloaliphatic groups or by halogen atoms, such as 3-bromo-2,4-pentadionato-ruthenium (III) or 1,1,1-trifluoro-2,4-pentadionato-ruthenium (III), the glyoximates, quinoleinates and salicyaldehydates, and the derivatives of ethylenediamine, $\alpha,\alpha'$-dipyridyl and o-phenanthroline are also suitable. Another class of catalysts which is particularly suitable consists of the complexes formed by ruthenium derivatives with electron donors. Such complexes are obtained by using halogenated, carbonylated or nitrosylated derivatives of ruthenium as derivatives or ruthenium and, as electron donors, substances having lone pairs of electrons, such as phosphines, arsines, stibines or amines, or substances capable of forming structures having lone pairs of electrons and thus being able to act as electron donors. In particular, the complexes formed by the electron donors specifically quoted in French Patent Specification No. 1,337,558 may be used. Suitable complexes are those produced by reaction of ruthenium compounds, particularly halides and hydridohalides, with aliphatic or cycloaliphatic monoolefines and diolefines, such as for example butadiene, isoprene or cyclooctadiene, with activated olefines such as acrylic or methacrylic derivatives such as acrolein, methacrolein or acrylamide, with saturated or unsaturated, aliphatic, cycloaliphatic or aromatic nitriles such as acetonitrile, propionitrile, acrylonitrile, methacrylonitrile, cyanocyclohexane, benzonitrile or toluonitrile, with saturated or unsaturated dinitriles such as malonitrile, succinonitrile, adiponitrile, dicyanobutanes, dicyanocyclobutanes or dicyanobutenes, or with aliphatic or aromatic isonitriles. Such complexes may be prepared by heating a ruthenium halide with the electron donor, optionally in the presence of a solvent which may itself participate in the preparation of the complex.

To carry out the new process, a weight of catalyst corresponding to a weight of metallic ruthenium from 0.04 to 1.2% of the weight of the acrylonitrile which is treated is generally suitable. However these limits are not rigid and for particularly reactive ruthenium derivatives, such as ruthenium trichloride or ruthenium acetylacetonate, lower proportions corresponding to, for example, 0.01% or even 0.001% of metallic ruthenium may be used. These catalysts may be used in the solid state, in finely divided form, in suspension, or in solution in water or an organic solvent which is inert under the reaction conditions. The catalysts do not change, or change only very slightly, during the reaction and can be re-used for a certain number of operations without it being necessary to regenerate them each time.

The reaction must be carried out in the presence of hydrogen which may be introduced all at once or in several stages, or even continuously to maintain a constant pressure of hydrogen. The pressure and temperature may vary within certain limits, most generally 1 to 50 bars in the case of the pressure and 50°C. to 150°C. in the case of the temperature. It is not advantageous to work outside these limits. Below the lower values quoted above, the the reaction proceeds only very slowly, whilst above the upper above-mentioned values a considerable quantity of propionitrile is formed by direct hydrogenation of the acrylonitrile, to the detriment of the desired products. The most advantageous operating conditions generally lie within the range of 5 to 40 bars for the pressure and 100°–130°C. for the temperature. Depending on the operating conditions, either the 1,4-dicyano-butenes or adiponitrile, or a mixture of them, is obtained. To obtain the 1,4-dicyano-butenes to the exclusion of the adiponitrile, or at least accompanied by as little adiponitrile as possible, it is advantageous to operate at low hydrogen pressures. The reaction can also be restricted to the formation of 1,4-dicyano-butenes by lowering the reaction temperature or by reducing the duration of heating. The reaction can also be oriented towards the formation of dicyano-butenes by selecting a catalyst of low activity or by using a more active catalyst in smaller amount, or by operating in a dilute medium.

To obtain solely, or almost solely, adiponitrile it is, conversely, advisable to use the hydrogen at a relatively higher pressure. It is possible to operate either with a single introduction of hydrogen if under the operating conditions (volume of apparatus and initial pressure) the pressure, which declines, nevertheless at all times remains sufficiently high to produce the desired result, or preferably to operate with repeated additions or continuous feed of hydrogen in order constantly to maintain the hydrogen pressure at the appropriate value. At a given pressure the reaction can also be oriented towards the preponderant formation of adiponitrile by increasing the temperature, the activity of the catalyst, and its concentration in the reaction mixture. Thus both for the formation of 1,4-dicyano-butenes and for the formation of adiponitrile there exists a narrow correlation between the operating conditions and it is possible in certain cases to obtain a mixture of the two dinitriles rather than one or other of them. Such mixtures may be subjected to a catalytic hydrogenation in order to convert them quantitatively into adiponitrile, as may also be done with 1,4-dicyano-butene alone.

The acrylonitrile employed in the reaction may be either commercial acrylonitrile, or freshly distilled and unstabilised acrylonitrile, or distilled acrylonitrile to which very small quantities of a stabiliser, such as hydroquinone, p-butyl-pyrocatechol, p-nitroso-dimethylaniline or ammonia, have been added.

The reaction may be carried out in the presence or absence of an auxiliary diluent which is liquid and inert under the operating conditions. Water, alcohols such as methanol or ethanol, glycols, glycol ethers such as methoxy-ethanol, diglyme, cyclic ethers such as dioxane and tetrahydrofurane, aliphatic, cycloaliphatic or aromatic hydrocarbons such as benzene or cyclohexane, nitriles such as acetonitrile and propionitrile, nitrated derivatives and amides are suitable diluents.

When the reaction has ended, the unconverted acrylonitrile may be isolated by distilling from the reaction mixture, at 80°–100°C. and normal pressure, the solvent and the propionitrile which is the only volatile by-product formed. The 1,4-dicyano-butenes and/or the adiponitrile are then separated by distillation in vacuo. The catalyst may be separated from the reaction mixture by any known means and may be recycled.

The following Examples illustrate the invention and show the effect of varying the different factors.

EXAMPLE 1

400 g. of acrylonitrile stabilised with 0.5% of hydroquinone, 2 g. of ruthenium chloride and varying quantities of Ru O (OH)$_2$ are introduced into a 1.5-liter stainless steel autoclave equipped with an anchor stirrer, a heating system and a device for regulating the pressure. The contents of the autoclave are maintained at 110°C. for 7 hours 30 minutes under a constant hydrogen pressure of 10 bars. After releasing the gas, the reaction mixture is distilled in vacuo. The results listed in the table below are obtained:

| Quantity of Ru O(OH)$_2$ in g. | Yield of dimers based on acrylonitrile converted in % | Degree of conversion of acrylonitrile, in % |
|---|---|---|
| 0 | 56.3 | 45.7 |
| 0.02 | 55.8 | 54.2 |
| 0.04 | 57.6 | 73.5 |
| 0.1 | 58.9 | 83.2 |
| 0.2 | 58.2 | 97.4 |

The Ru O(OH)$_2$ is prepared in the following manner. Potassium ruthenate is first prepared by heating to 400°C. in a silver crucible in a stream of air at 60 l/hour a mixture of 3 g. of ruthenium, 30 g. of KOH pellets, and 3 g. of KNO$_3$. After 1 hour 30 minutes heating, the mixture is cooled, and the residue is taken up in 50 cm$^3$ of water and a slight amount of insoluble matter is removed by filtration. The filtrate containing K$_2$ RuO$_4$ is heated to 50°C., 77 cm$^3$ of an aqueous solution containing 7.1 cm$^3$ of methanol are then added over the course of 15 minutes, and heating at 50°C. is continued for a further 15 minutes. The mixture is cooled and filtered, and the residue is washed first with 30 cm$^3$ of 15% strength HNO$_3$, and then with water until neutral, and dried in vacuo. 4.42 g. of a product the percentage analysis of which corresponds to Ru O(OH)$_2$ are obtained [a yield of 98.45%].

EXAMPLE 2

80 g. of acrylonitrile stabilised with 0.04 of hydroquinone, 0.4 g. of ruthenium chloride, and varying quantities of Ru (OH)$_3$ are introduced into a 250 cm$^3$ stainless steel autoclave equipped as in Example 1. The contents of the autoclave are heated to 120°C. for 6 hours 30 minutes under a constant hydrogen pressure of 10 bars. After releasing the gas, the reaction mixture is distilled. The results listed in the table below are obtained:

| Weight of Ru (OH)₃) | Yield of dimers based on acrylonitrile converted, | Degree of conversion of acrylonitrile, in |
|---|---|---|
| in g. | in % | % |
| 0 | 55 | 67.4 |
| 0.008 | 52.6 | 88.2 |
| 0.020 | 56.7 | 96.2 |

Ru (OH)₃ is prepared by heating under reflux a mixture of 1 g. of ruthenium chloride and 28 cm³ of a 5% strength aqueous solution of potassium bicarbonate. The precipitate which forms is filtered off, washed with 10 cm³ of water, and dried. The percentage analysis corresponds to the compound of formula Ru (OH)₃.

EXAMPLE 3

160 g. of acrylonitrile stabilised with 0.08 g. of hydroquinone, 0.8 g. of tris(acetylacetonato)rutheniun, and varying quantities of Ru O(OH)₂ are introduced into a 750 cm³ autoclave equipped as in Example 1. The contents of the autoclave are kept at 130°C., under a constant hydrogen pressure of 10 bars, for 7 hours 30 minutes. After distilling the reaction mixture, the results listed in the table below are obtained:

| Weight of Ru O(OH)₂ in g. | Products formed | proportion of adiponitrile in the products formed, in % | Yields of dimers based on acrylonitrile converted in % | Degree of conversion of acrylonitrile in % |
|---|---|---|---|---|
| | in g. | | | |
| 0.008 | 62.2 | 12 | 57.6 | 67.1 |
| 0.012 | 87 | 15 | 58.2 | 92.5 |
| 0.016 | 87.3 | 24 | 55 | 99 |
| 0.032 | 86.5 | 40 | 53.4 | 99 |
| 0.080 | 83.3 | 57 | 51.6 | 99 |

Increasing the quantity of Ru O(OH)₂ results in an increase in the degree of conversion of the acrylonitrile and in the quantity of adiponitrile formed.

EXAMPLE 4

80 g. of acrylonitrile stabilised with 0.040 g. of hydroquinone, 0.661 g. of a complex of formula RuCl₂ (C₄H₆)₃ [(2,6,10-dodecatrienediyl-1,12)dichlororuthenium] and varying quantities of Ru O(OH)₂ are introduced into a 250 cm³ autoclave equipped as in Example 1. The contents of the autoclave are raised to 110°C. under a constant hydrogen pressure of 10 bars. After distilling the reaction mixture, the following results are obtained:

| Weight of Ru O(OH)₂ in g. | Duration of reaction | Yields of dimers based on acrylonitrile converted, in % | Degree of conversion of acrylonitrile, in % |
|---|---|---|---|
| 0 | 8 hrs. | 58 | 66 |
| 0.020 | 6 hrs. 10 mins. | 58 | 64 |
| 0.040 | 4 hrs. 45 mins. | 57 | 71 |

EXAMPLE 5

The procedure of Example 4 is followed, but replacing the complex of formula RuCl₂(C₄H₆)₃ by 0.736 g. of trichlorotris(acetonitrile)-ruthenium (that is to say 0.200 g. of ruthenium) and replacing the Ru O(OH)₂ by platinum deposited on charcoal (charcoal with 4.7% of platinum). After distilling the reaction mixture, the following results are obtained:

| Weight of catalyst containing 4.7% of Pt in g. | Duration of reaction | Yield of dimers based on acrylonitrile converted, in % | Degree of conversion of acrylonitrile in % |
|---|---|---|---|
| 0 | 7 hrs. 30 mins. | 59 | 73 |
| 0.100 | 4 hrs. 30 mins. | 59 | 68 |

EXAMPLE 6

The procedure of Example 4 is followed, but using 0.760 g. of dichlorotetrakis(acrylonitrile)ruthenium as the catalyst and varying quantities of Ru O(OH)₂ as the activator. After treatment of the reaction mixture, the following results are obtained:

| Quantity of Ru O(OH)₂ in g. | Duration of reaction | Yield of dimers based on acrylonitrile converted, in % | Degree of conversion of acrylonitrile, in % |
|---|---|---|---|
| 0 | 6 hrs. 30 mins. | 60 | 76 |
| 0.020 | 4 hrs. 30 mins. | 60 | 71 |
| 0.040 | 4 hrs. 7 mins. | 59 | 78 |

What is claimed is:
1. In a process for converting acrylonitrile to its straight chain linear di-cyano dimer or its straight chain linear di-cyano hydrodimer which comprises dimerizing acrylonitrile in the presence of molecular hydrogen at a temperature of 50°C to 120°C under a hydrogen pressure of 1 to 50 bars and
in the presence of a catalyst selected from the group
consisting of ruthenium salts of mineral and organic acids, complexes formed between a ruthenium halide and an electron donor and ruthenium chelate complexes, the improvement which comprises adding a catalyst activator to the reaction mixture in an amount of 1 to 25%, calculated as metal of the weight of the ruthenium introduced by said catalyst wherein said catalyst activator is selected from the group consisting of metallic ruthenium, metallic platinum, metallic nickel, metallic rhodium, $RuO_2$, $RuO(OH)_2$ and $Ru(OH)_3$.

2. The process of claim 1 wherein said activator is a metal supported on a carrier inert under the reaction conditions.

3. The process of claim 1 wherein said catalyst is ruthenium chloride.

4. The process of claim 1 wherein said catalyst is tris(acetylacetonato)ruthenium.

5. The process of claim 1 wherein said catalyst is (2,6,10-dodecatrienediyl-1,12)dichloruthenium.

6. The process of claim 1 wherein said catalyst is trichlorotris(acetonitrile)-ruthenium.

7. The process of claim 1 wherein said catalyst is dichlorotetrakis(acrylonitrile)ruthenium.

8. The process of claim 1 wherein said temperature is from 100° to 130°C.

9. The process of claim 1 wherein said pressure is from 5 to 40 bars.

* * * * *